United States Patent [19]
Schellino et al.

[11] Patent Number: 5,775,898
[45] Date of Patent: Jul. 7, 1998

[54] ORTHODONTIC SCREW FOR A FAST EXPANSION ON THE ANTERIOR SECTOR OF THE MAXILLARY ARCH

[75] Inventors: Eleonora Schellino, Vinovo; Modica Remo, Turin, both of Italy

[73] Assignee: Leone S.p.A., Fiorentino, Italy

[21] Appl. No.: 773,959

[22] Filed: Dec. 26, 1996

[51] Int. Cl.⁶ .................................................. A61C 3/00
[52] U.S. Cl. ............................................................... 433/7
[58] Field of Search ........................................... 433/7

[56] References Cited

U.S. PATENT DOCUMENTS

| | | | |
|---|---|---|---|
| 3,977,082 | 8/1976 | Siatkowski | 433/7 |
| 4,348,179 | 9/1982 | Nardella | 433/7 |
| 4,482,318 | 11/1984 | Forster | 433/7 |

FOREIGN PATENT DOCUMENTS 981973  6/1951  France ...................................... 433/7

Primary Examiner—John J. Wilson
Attorney, Agent, or Firm—McGlew and Tuttle

[57] ABSTRACT

The apparatus for obtaining an at least prevailing or even exclusive expansion in the anterior sector of the maxillary arch two substantially symmetrical components (1, 3) with arms (11, 12; 31, 32) fan-like stretching apart and to be combined with orthodontic bands (40); the two components (1, 3) are articulated to one another by means of a hinge (5); an expansion screw (7) acting between the two components (1, 3) is able to stretch them angularly apart by progressive actions to be exerted on the same screw.

10 Claims, 3 Drawing Sheets

ORTHODONTIC SCREW FOR A FAST EXPANSION ON THE ANTERIOR SECTOR OF THE MAXILLARY ARCH

FIELD OF THE INVENTION

The present invention refers to an apparatus, that is, an orthodontic screw, for obtaining an expansion of the upper maxillary arch, the screw being able to cause a prevailing or exclusive expansion, especially of fast type, of the anterior arch alone. Palates have often been found to exhibit very small transverse diameters in the anterior sector arch and almost normal diameters in the molar arch. In these cases, it is not possible to apply a traditional fast expansion screw which stretches apart with a parallel movement, as it would imply an increase of both the anterior and posterior, that is molar, diameters.

The invention refers to an apparatus allowing only the expansion in the anterior sector, which has proven to be very useful in such cases as LPS (PALATE-LABIAL SCHISTASIS), alteration of transverse diameters during children's growth and, in adults, after corticotomy.

SUMMARY OF THE INVENTION

The present orthodontic apparatus comprises two substantially symmetrical components, with arms, mostly fan-like stretching apart, to be combined with orthodontic bands or equivalent means, and hinged to one another. An expansion screw (7) acting between the two components (1, 3) is able to stretch the components angularly apart by progressive actions exerted on the screw so as to act at least in a prevailing way on the anterior maxillary arch.

The screw is advantageously engaged with bushes articulated to the two components in such a way as to ensure the alignment thereof with the same screw. Once the apparatus is in use, each of the two components articulated to one another has its arms oriented forwards with respect to the hinge, the arms being able to be modelled for their anchoring by orthodontic bands or other equivalent means.

Either or both components may have at least two arms.

Additional advantages, features and details of the invention result from the following description as well as the attached drawings of a preferred embodiment of the orthodontic expansion screw.

DESCRIPTION OF THE PREFERRED EMBODIMENTS

Figure 1:
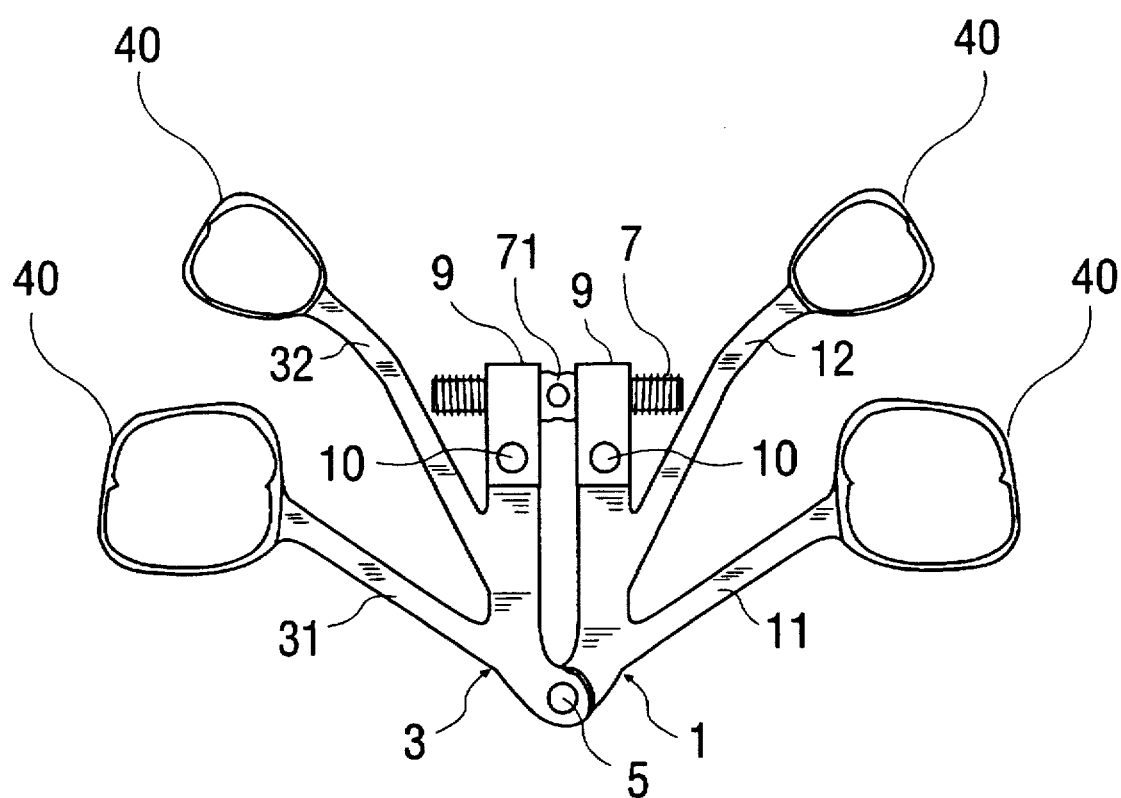
FIG. 1 shows a front view of the orthodontic screw combined with the bands prior to the use.
Figure 2:
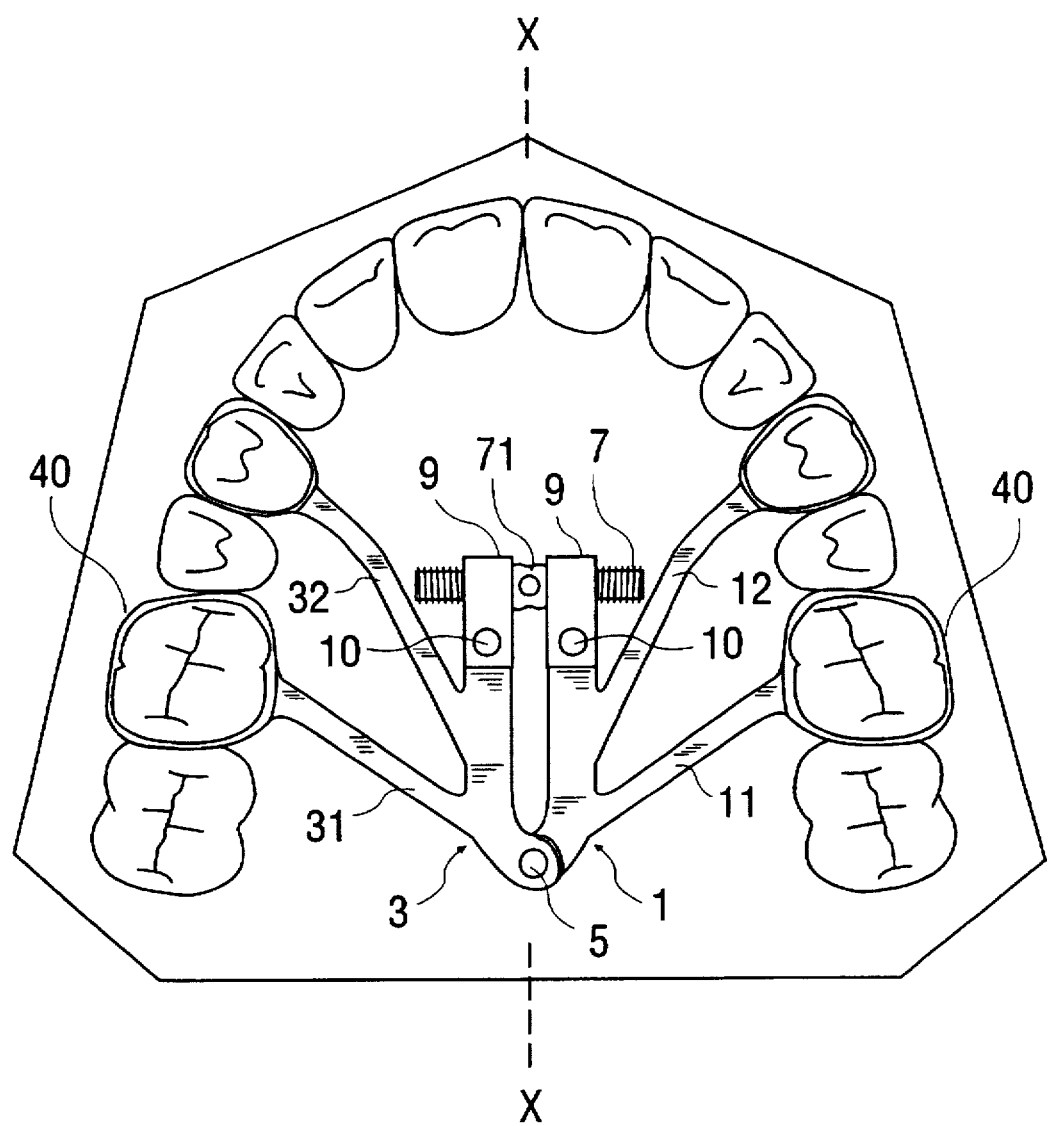
FIGS. 2 and 3 show the orthodontic screw in use in the maxillary arch before and respectively after the stretsching apart of the above-mentioned components.
Figure 3:
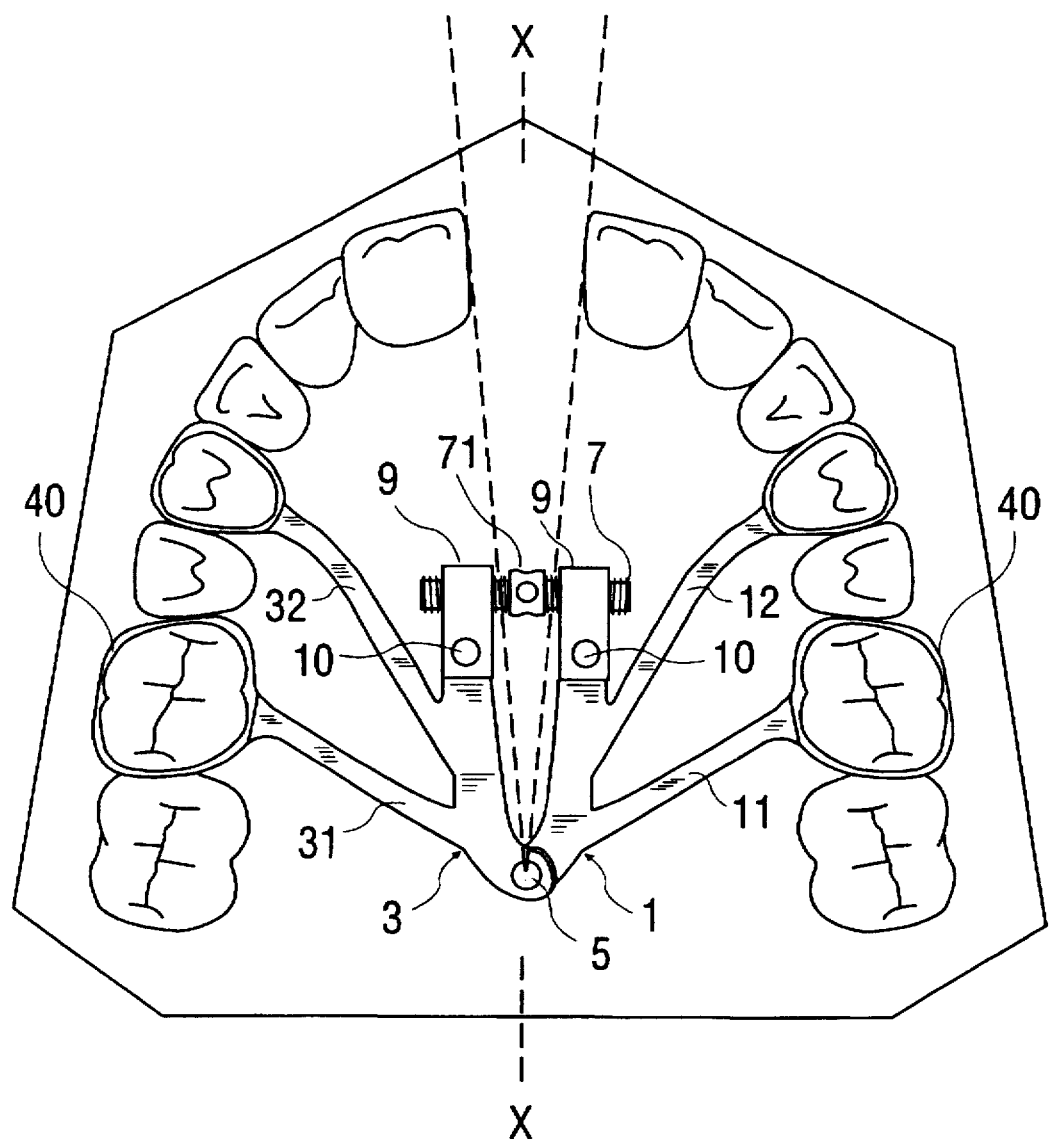

According to the present invention, reference being made to the figures of the accompanying drawings, the apparatus comprises of two components 1 and 3, each of which is provided with two arms 11 and 12, respectively 31 and 32, having a substantial radial development with respect to the whole of the two components 1 and 3. The two components are articulated to a hinge 5 which is posteriorly located in the maxillary arch. The arms 11, 31, and 12, 32 are substantially symmetrical with respect to the sagittal plane X—X; the arms 11 and 31 are inclined indicatively of about 75° to the axis X—X, while the arms 12 and 32 are inclined of a smaller angle with respect to the axis X—X. Provided at a limited distance from the articulation 5 and anteriorly located, is an expansion screw 7 provided with radial seats, which is symmetrically operable by a tool for a direct intervention on the apparatus in use. The two threaded lengths of the screw 7 engage within bushes 9 which are articulated to the components 1 and 3 at points 10, so as to ensure the alignment of the bushes 9 and thus of their threaded holes with the axis of the screw 7, in any mutual angular position of the two components 1 and 3 about the hinge 5, as obtained by acting on the screws 7, when changing the angle thereof with respect to the sagittal plane X—X.

The foreward orientation of the posterior anchorages of arms 11 and 31 obtained by acting on the screw 7, brings about a slightly increased spacing thereof, accompanied by no, or at least a very limited, reduction of the posterior diameters, or even a slight expansion of the inter-first molar diameter and, to a lesser extent, of the inter-second molar. The arms 12 and 32 are mostly intended for application on premolars or canines, while the arms 11 and 31 are for application on far posterior teeth.

The arms 11, 31 and 12, 32 can be modelled extemporarily and are apt to be welded to orthodontic bands such as those roughly indicated at 40, or to other equivalent means for the anchorage of the anterior maxillary arch, to achieve an at least prevailing or even exclusive expansion of the anterior sector, for the abovementioned purposes. The modelling of the apparatus will be performed according to the dimensional and morphological characteristics of the maxillary arch of the patient.

Once the apparatus, that is the orthodontic screw, is in use, the components 1 and 3 being substantially brought close to one another when the apparatus is positioned the first time in the oral cavity of the patient, by moving the components 1 and 3 angularly towards the sagittal plane X—X, a frequent intervention is carried out on the screw 7 and, in particular, on its core 71, to stretch apart the two components 1 and 3 about the articulation 5, thereby causing the stresses necessary to induce the corrections required by the apparatus in question.

As for the traditional fast expansion screw, it is possible to test the bands on the first or second molars, depending on the case and possibility, and on the first premolars. After taking a position impression, the arms are welded to the bands and rounded or anyway adapted according to the production process.

With children, after cementation, the expansion is operated through a half or a quarter of revolution per day and, within eight-fifteen days. The desired expansion is obtained together with a prevailing palatine suture detachment in the anterior sector. In adult patients, the expansion is to be associated to the corticotomy, so as to achieve the desired expansion also in these cases.

The apparatus may be applied even to a patient having palate-labial schistasis, in which case a widening of the anterior diameters and a subsequent alignment is obtained.

It is understood that the drawing shows only a practical exemplification of the invention, as this may vary in the forms and dispositions without nevertheless departing from its scope. The reference numbers in the attached claims are intended to facilitate the reading thereof in connection with the description and the drawing, and does not limit the scope of the claims.

We claim:

1. An orthodontic apparatus for expanding the maxillary arch of a patient, comprising:

a first component with arm stretching outwardly toward one side in a fan-like arrangement;

a second component with arms stretching outwardly toward another side in a fan-like arrangement;

arms extending from said first and second components to the maxillary arch when in use;

a hinge, said first component and said second component being articulated to said hinge to form an articulated arrangement which is substantially symmetrical;

anchorage means for anchoring said fan like arms of said first component to the anterior maxillary arch of a patient and for anchoring said fan like arms of said second component to the anterior maxillary arch; and fast expansion orthodontic screw means acting between said two components for moving said first component and said second component angularly apart by progressive action on the screw for one of a prevailing or exclusive expansion in the upper maxillary arch anterior sector of the patient.

2. The orthodontic apparatus according to claim 1, wherein said screw means includes a screw element engaged with bushes and articulation means for articulating one of said bushes to said first component and articulating another of said bushes to said second component to ensure the alignment of threaded portions of said bushes with said screw element.

3. The orthodontic apparatus according to claim 1, wherein said arms of each of said first component and said second component extended in a forward direction with respect to said hinge, when the apparatus is in an applied position.

4. The orthodontic apparatus according to claim 3, wherein each of said components is provided with two arms.

5. The orthodontic apparatus according to claim 1, wherein said anchorage means includes orthodontic bands connected to said arms at outer ends of said arms, said anchorage means cooperating with said first component, said second component, said hinge and said screw means for expansion in the upper maxillary arch anterior sector substantially without movement of connected teeth within associated sockets.

6. An orthodontic apparatus for expanding the maxillary arch of a patient, comprising:

a first component with a base portion and first and second arms stretching outwardly toward one side in a fan-like arrangement;

a second component with a base portion and first and second arms stretching outwardly toward another side in a fan-like arrangement;

said arms extending from said first and second components to the maxillary arch when in use;

a hinge, said first component and said second component being articulated to said hinge at a base inward end, said arms of each of said first component and said second component extending in a forward direction with respect to said hinge, when the apparatus is in an applied position, said inward end being opposite from a direction of said outwardly stretching arms, said inward end being posteriorly located in the maxillary arch, said hinge and said first component and said second component forming an articulated arrangement which is substantially symmetrical;

anchorage means for anchoring said fan like arms of said first component to the anterior maxillary arch of a patient and for anchoring said fan like arms of said second component to the anterior maxillary arch; and fast expansion orthodontic screw means acting between said two components for moving said first component and said second component angularly apart by progressive action on the screw for one of a prevailing or exclusive expansion in the upper maxillary arch anterior sector of the patient.

7. The orthodontic apparatus according to claim 6, wherein said screw means includes a screw element engaged with bushes and articulation means for articulating one of said bushes to said first component base portion and articulating another of said bushes to said second component base portion to ensure the alignment of threaded portions of said bushes with said screw element.

8. The orthodontic apparatus according to claim 6, wherein said anchorage means includes orthodontic bands connected to said arms at outer ends of said arms, said anchorage means cooperating with said first component, said second component, said hinge and said screw means for expansion in the upper maxillary arch anterior sector substantially without movement of connected teeth within associated sockets.

9. An orthodontic apparatus for expanding the maxillary arch of a patient, comprising:

a first component with a base portion and first and second fan-like arms stretching outwardly toward one side in a fan-like arrangement;

a second component with a base portion and first and second fan-like arms stretching outwardly toward another side in a fan-like arrangement;

said arms extending from said first and second components to the maxillary arch when in use;

a hinge, said first component and said second component being articulated to said hinge at a base inward end, said arms of each of said first component and said second component extending in a forward direction with respect to said hinge, when the apparatus is in an applied position, said inward end being opposite from a direction of said outwardly stretching arms, said inward end being posteriorly located in the maxillary arch, said hinge and said first component and said second component forming an articulated arrangement which is substantially symmetrical with respect to a sagittal plane of the patient;

anchorage means for anchoring said fan like arms of said first component to the anterior maxillary arch of a patient and for anchoring said fan like arms of said second component to the anterior maxillary arch; and fast expansion orthodontic screw means acting between said two components for moving said first component and said second component about said hinge, angularly apart by progressive action on the screw for one of a prevailing or exclusive expansion in the upper maxillary arch anterior sector of the patient, said screw means including a screw element engaged with bushes and articulation means for articulating one of said bushes to said first component base and articulating another of said bushes to said second component base to ensure the alignment of threaded portions of said bushes with said screw element.

10. The orthodontic apparatus according to claim 9, wherein said anchorage means includes orthodontic bands connected to said arms at outer ends of said arms, said anchorage means cooperating with said first component, said second component, said hinge and said screw means for expansion in the upper maxillary arch anterior sector substantially without movement of connected teeth within associated sockets.

* * * * *